United States Patent [19]
Garry et al.

[11] Patent Number: 5,669,380
[45] Date of Patent: Sep. 23, 1997

[54] LARYNGEAL BYPASS

[75] Inventors: Brendan P. Garry, Westborough; Peak Woo, Weston, both of Mass.

[73] Assignee: New England Medical Center Hospitals, Inc., Boston, Mass.

[21] Appl. No.: 639,167

[22] Filed: Apr. 26, 1996

[51] Int. Cl.$^6$ .................................................. A61M 16/00
[52] U.S. Cl. ................... 128/207.14; 128/207.15
[58] Field of Search .................. 128/207.11, 207.12, 128/207.14, 207.29; 604/163, 171, 192

[56] References Cited

U.S. PATENT DOCUMENTS

| | | | |
|---|---|---|---|
| 3,788,326 | 1/1974 | Jacobs | 128/204.14 |
| 4,627,433 | 12/1986 | Lieberman | 128/204.14 |
| 4,796,617 | 1/1989 | Matthews et al. | 128/204.14 |
| 5,029,580 | 7/1991 | Radford et al. | 128/204.14 |
| 5,186,167 | 2/1993 | Kolobow | 128/204.14 |
| 5,269,769 | 12/1993 | Dhara et al. | 128/204.14 |
| 5,544,648 | 8/1996 | Fischer, Jr. | 128/204.14 |

OTHER PUBLICATIONS

Jacobs, M.D., "Emergency Percutaneous Transtracheal Catheter and Ventilator", *The Journal of Trauma*, vol. 12, No. 1, (Jan. 1972) pp. 50–55.

Schragl et al., "Superimposed High–Frequency Jet Ventilation via the Jet Laryngoscope for Tracheotomy due to a 5-cm Massive Stenosis of the Larynx", *Laryngo–Rhino–Otologie*, vol. 74, Apr. 1995, pp. 223–226.

Strashnov et al., "High Frequency Jet Ventilation in Endoplaryngeal Surgery", *Journal of Clinical Anesthesia*, vol. 7, No. 1, Jan./Feb. 1995, pp. 19–25.

Depierraz et al., "Percutaneous transtracheal jet ventilation for paediatric endoscopic laser treatment of laryngeal and subglottic lesions", *Canadian Journal of Anaesthesia*, 41 (12), 1994, pp. 1200–1207.

Bourgain et al., "Measurement of End–expiratory Pressure During Transtracheal High Frequency Jet Ventilation for Laryngoscopy", *British Journal of Anaesthesia*, 65 (6), 1990, pp. 737–743.

Klain et al., "High Frequency Jet Ventilation", *Surg Clin North Am*, 65 (4), Aug. 1985, pp. 917–930.

*Primary Examiner*—Vincent Millin
*Assistant Examiner*—Robert N. Wieland
*Attorney, Agent, or Firm*—Testa, Hurwitz & Thibeault, LLP

[57] ABSTRACT

A laryngeal bypass device for transcutaneous insertion into a human sublaryngeal trachea has an outer tubular member coupled to an aspiration device and an inner tubular member disposed within the outer tubular member and coupled to a ventilation device. The inner tubular member delivers oxygenated air from the ventilation device to the lungs, and the outer tubular member aspirates carbon dioxide from the lungs. By utilizing the two tubular members in a single bypass device, adequate ventilation of the lungs occurs without the need for air evacuation through the mouth, as the larynx is completely bypassed. In one embodiment, the laryngeal bypass device further includes a barrier member coupled to the inner tubular member for maintaining the outer and inner tubular members free of surrounding tissue during respiration. In another embodiment, an inflatable cuff encircles the outer tubular member to block the flow of air from the trachea to the larynx, thereby enhancing respiration while preventing interference with a surgical procedure that may be taking place in the area of the larynx.

42 Claims, 9 Drawing Sheets

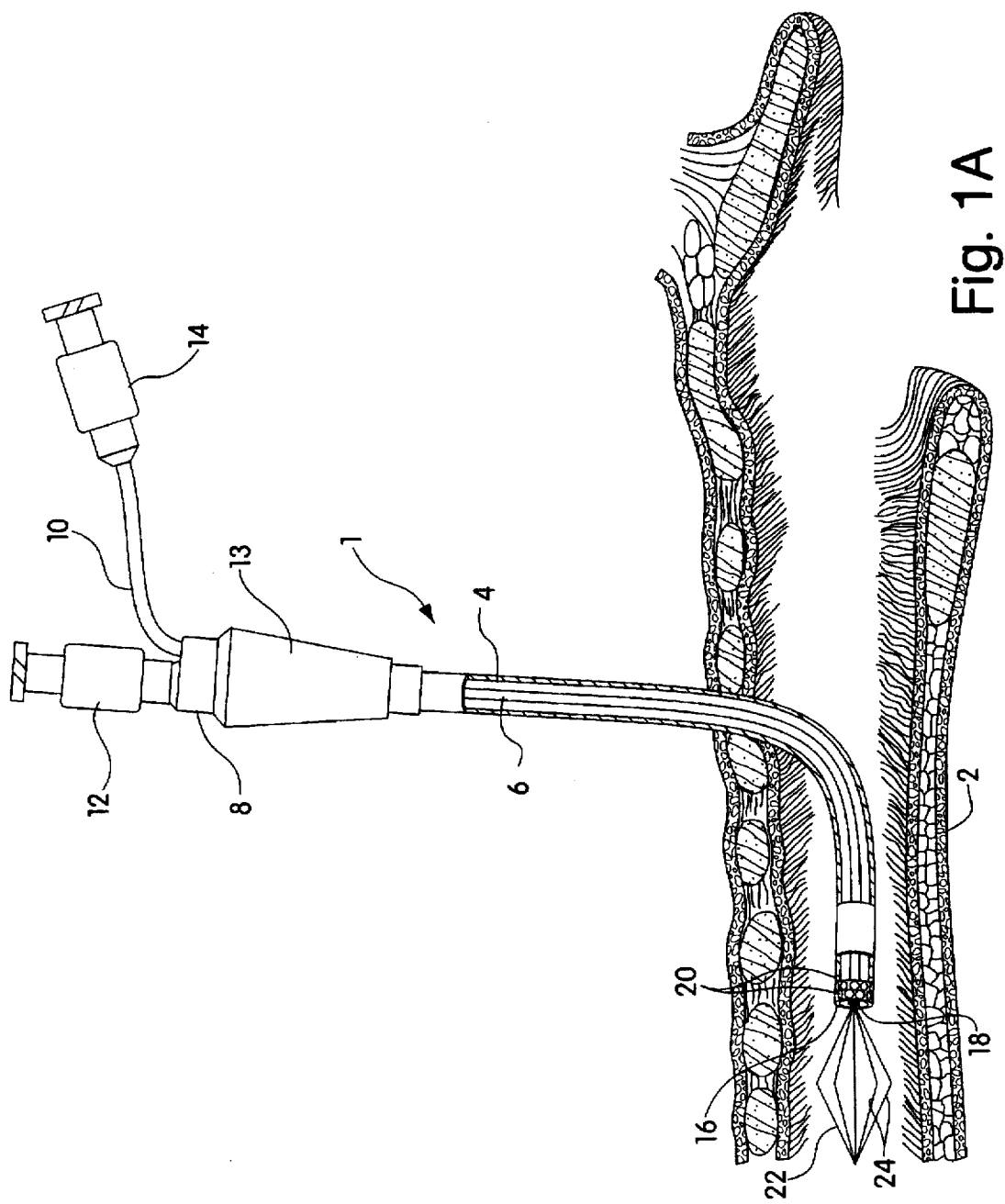

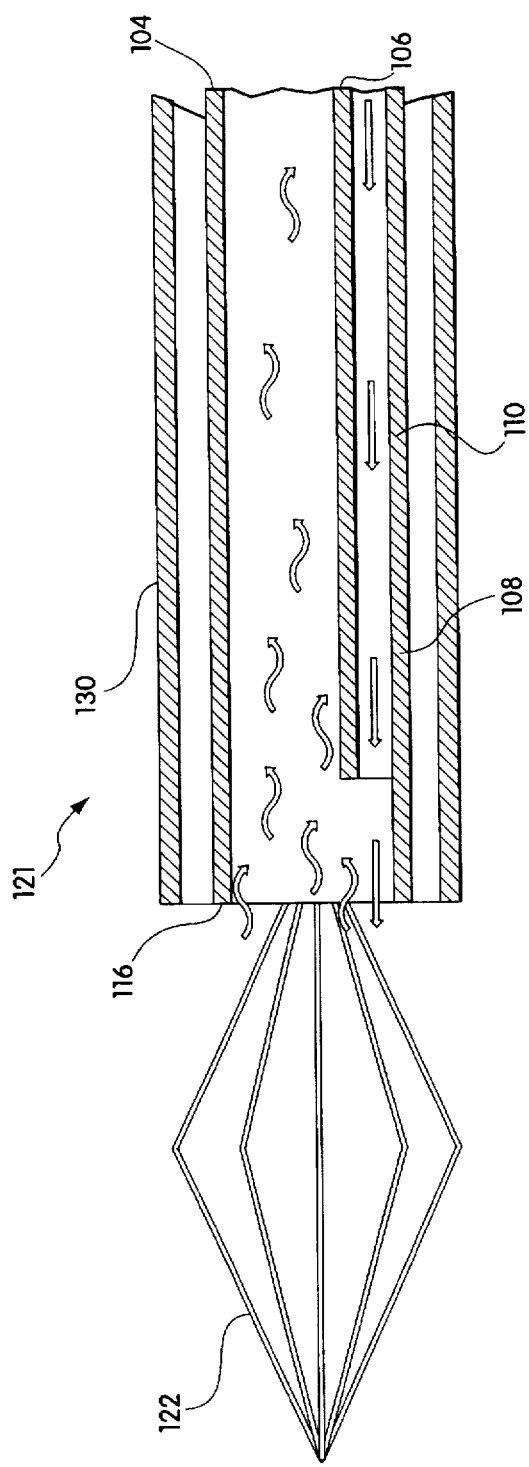
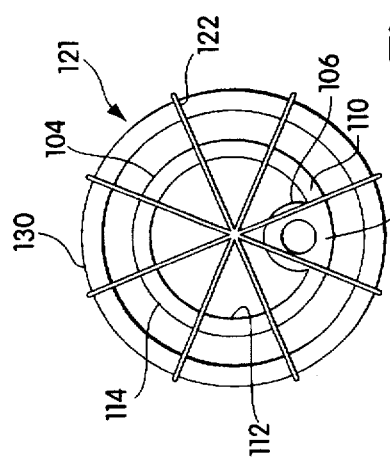
Fig. 4A
Fig. 4B

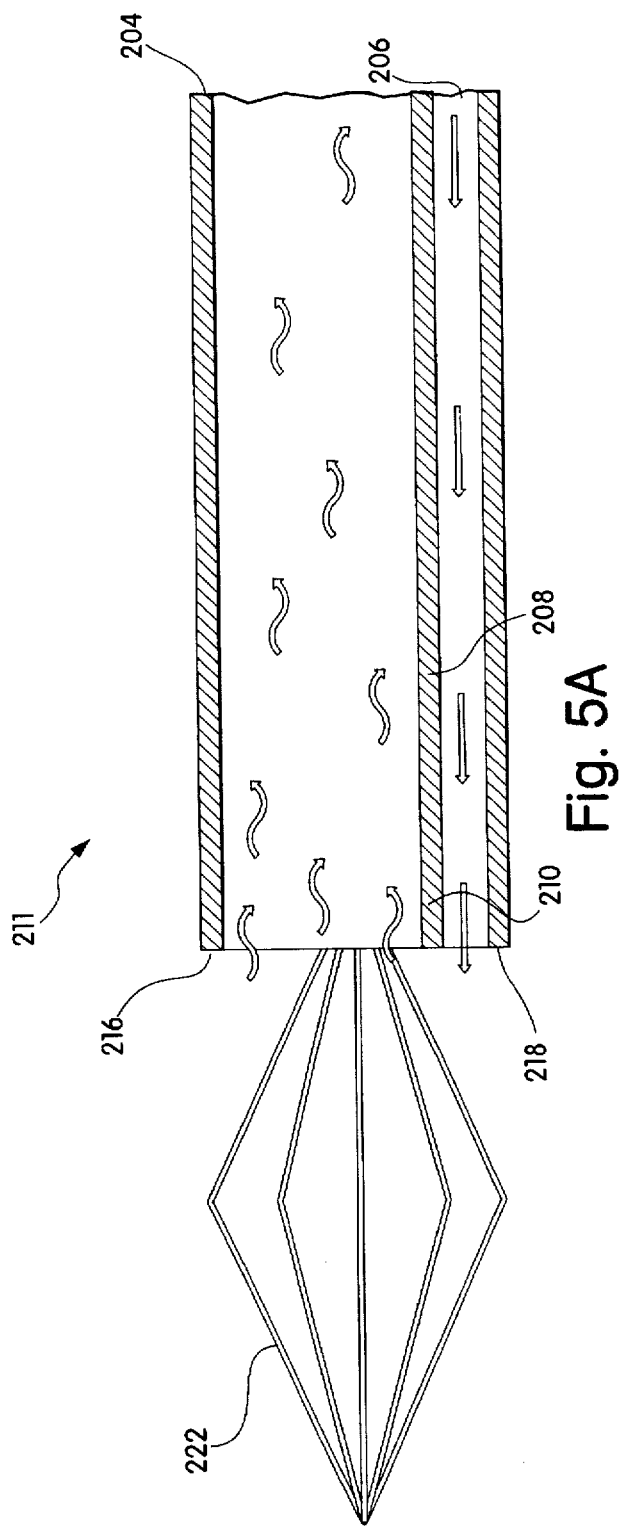
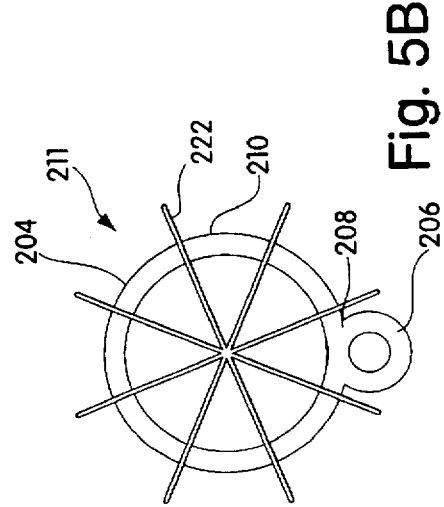
Fig. 5A
Fig. 5B

LARYNGEAL BYPASS

TECHNICAL FIELD

This invention relates to a tracheal respiration device inserted sublaryngeally.

BACKGROUND INFORMATION

At the present time a tracheostomy is required to allow surgery to be performed on a stenosed larynx. Stenosis of the larynx is caused by cancer, trauma, fibrosis, cysts, arterial, venous or arteriovenous malformations, and other less common causes. Notwithstanding the natural adversity of patients in consenting to a tracheostomy, tissue damage and morbidity is high, hospitalization is prolonged, and subsequent phonation problems typically result.

Options to tracheostomy currently exist, one of which is a procedure known as venturi jet ventilation. This procedure is typically carried out with a catheter that is inserted into a laryngoscope or directly into the trachea to deliver a high pressure jet of air to inflate the lungs. Jet ventilation is utilized in emergency situations when a tracheostomy is not preferred or an endotracheal tube cannot be placed. This procedure can also be used during microlaryngoscopy to improve surgical access. The jetting catheters used for such a procedure are smaller than conventional endotrachial tubes. For example, jet ventilation is typically performed using a 14, 16, or 18 French (Fr) gauge (G) catheter.

There are several disadvantages to performing conventional jet ventilation. Among them are the problems of barotrauma, mucosal drying, gastric dilation, and the disturbing movement caused by the high pressure jet. Additionally, if egress of flow does not occur, complications such as outflow obstruction and pneumothorax may result. Moreover, monitoring of ventilation is difficult with jet ventilation as the pathway for exhausting the gas may be tenuous. Additionally, because the pressure in the lungs is very small by comparison to the high pressure jet, it is difficult to drive the gas out of the lungs. This can lead to "breath-stacking", where the next jet of gas increases the lung volume beyond its current volume. With no exhaust pathway through which to expel the gas, the lungs can easily and quickly rupture, a condition known as barotrauma. Jet ventilation is often terminated prematurely to prevent barotrauma from occurring.

SUMMARY OF THE INVENTION

It is an object of the invention to provide a minimally invasive respiration device that offers the advantages of tracheostomy tube ventilation, while avoiding the morbidity of a tracheostomy.

The present invention relates to a laryngeal bypass device for transcutaneous insertion into a human sublaryngeal trachea comprising a first tubular member and a second tubular member disposed within the first tubular member. One of the tubular members is coupled to an aspiration device to aspirate gas from the lungs, and the other tubular member is coupled to a ventilation device to deliver gas from the ventilation device to the lungs. By utilizing the two tubular members in a single bypass device, adequate ventilation of the lungs occurs without the need for expiration of gas through the mouth, as the larynx is completely bypassed. High pressure jets of gas are pushed into the lungs and subsequently pulled from the lungs, resulting in a novel "push-pull" effect which occurs simultaneously.

In one embodiment, the laryngeal bypass device further comprises a barrier member coupled to the second tubular member for maintaining the first and second tubular members free of surrounding tracheal tissue during respiration. In another embodiment of the present invention, an inflatable cuff encircles the first tubular member to block the flow of air from the trachea to the larynx, thereby enhancing respiration while preventing interference with a surgical procedure that may be taking place in the area of the larynx.

In still another embodiment of the present invention, an introducer and guidewire is disposed within the first tubular member for guiding the first and second tubular members into the trachea. In another embodiment of the present invention, the bypass device of the present invention includes a cannula to aid in transcutaneous insertion. In yet another embodiment of the invention, the laryngeal bypass has barrier elements and design characteristics that prevent tissue from entering the opening of the first tubular member during aspiration. In another embodiment of the invention, the first tubular member is coupled to a pressure monitor and the second tubular member is coupled to a carbon dioxide monitor.

In still another embodiment of the invention, the laryngeal bypass device utilizes a single tube for aspiration and ventilation. In this embodiment, high pressure jets of gas are alternately pushed into and pulled from the lungs via a single tube, resulting in a "push-pull" effect. The tube is coupled to a switching device such that when the switching device is in communication with a ventilation source, a jet of gas is delivered and no aspiration occurs. Similarly, when the switching device is in communication with the aspiration source, gas is drawn from the lungs and no ventilation occurs.

The present invention also relates to a method of using the laryngeal bypass device. The device is inserted transcutaneously into the sublaryngeal trachea, gas is delivered through one of the tubular members to inspirate the lungs, and gas is aspirated through the other tubular member.

Other objects of the present invention will become readily apparent to those skilled in this art from the following detailed description provided below. As will be realized, the invention is capable of other and different embodiments, and its details are capable of modifications within the scope and spirit of the present invention. Accordingly, the drawings and description are to be regarded as illustrative in nature, and not as restrictive.

BRIEF DESCRIPTION OF THE DRAWINGS

This invention is pointed out with particularity in the appended claims. The above and further advantages of this invention may be better understood by referring to the following description taken in conjunction with the accompanying drawings, in which:

FIG. 1A shows an embodiment of the laryngeal bypass device of the present invention transcutaneously inserted in the sublaryngeal trachea;

FIG. 4A shows an alternate embodiment of the laryngeal bypass device of the present invention wherein the ventilation tube is formed within the walls of the aspiration tube;

FIG. 4B is an end view of an alternate embodiment of the laryngeal bypass device of the present invention;

FIG. 5A shows an alternate embodiment of the laryngeal bypass device of the present invention wherein the ventilation tube is formed along the periphery of the aspiration tube;

FIG. 5B is an end view of an alternate embodiment of the laryngeal bypass device of the present invention;

DESCRIPTION

Figure 1B:
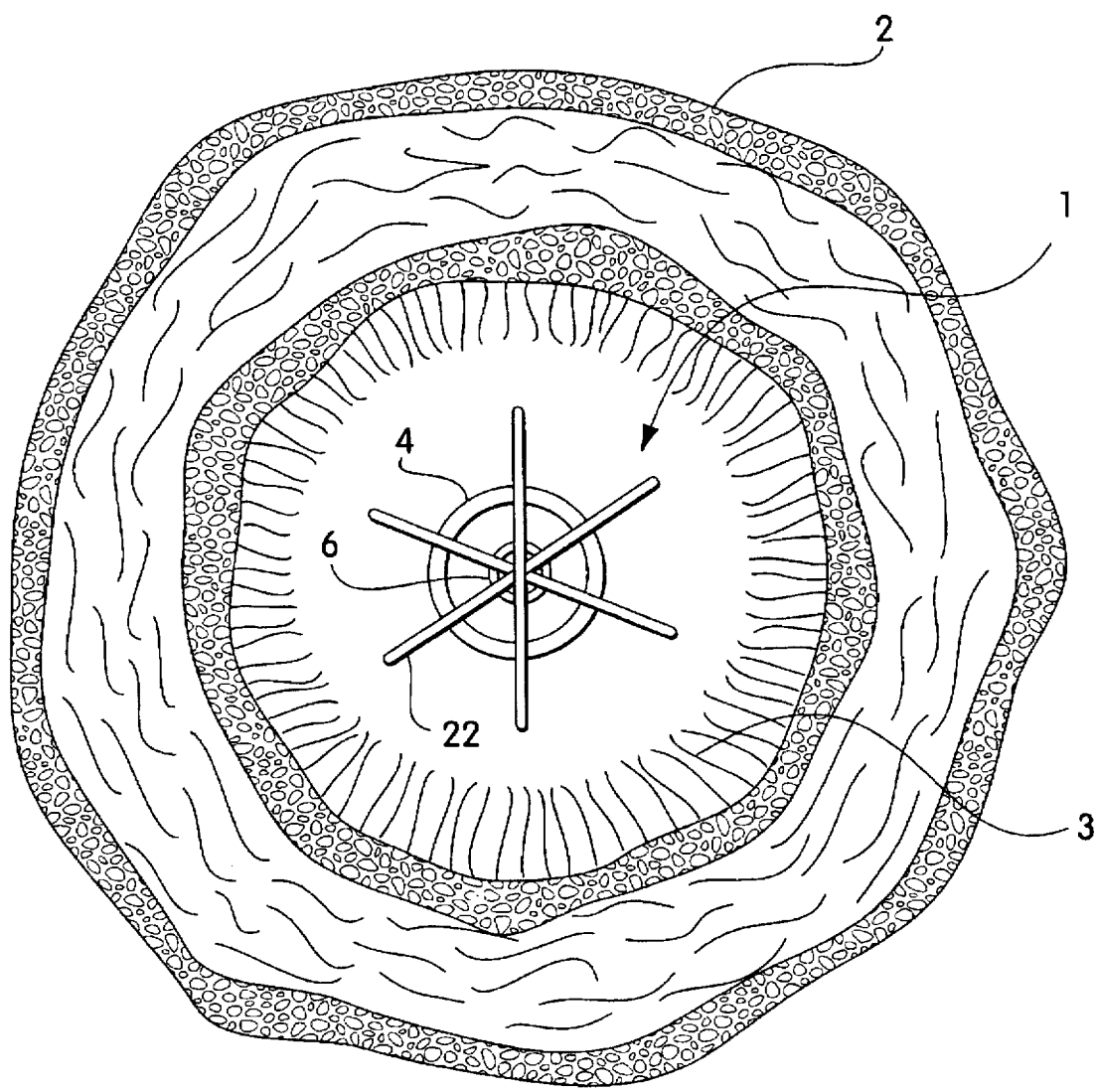
FIG. 1B is an end view of an embodiment of the laryngeal bypass device of the present invention.

Referring to FIG. 1A, a laryngeal bypass device 1 of the present invention is inserted into the sublaryngeal trachea 2. The laryngeal bypass device 1 in one embodiment comprises an outer aspiration tube 4 that encircles an inner jet ventilation tube 6. For clarity of description, these tubes will be referred to as an outer tube 4 and an inner tube 6 hereinafter. Although the outer and inner tubes, 4, 6 are shown as being round in shape, other shapes may be used, as long as a hollow lumen exists in the center of each tube 4, 6. By utilizing the two tubes 4,6 in a single bypass device 1, high pressure jets of gas are pushed into the lungs and pulled from the lungs, resulting in a novel "push-pull" effect which occurs simultaneously in this embodiment.

The outer tube 4 and the inner tube 6 can be fabricated of stainless steel, plastic, laser-resistant material, or other flexible material that is sufficiently strong to withstand the gas pressures involved, kink-resistant and biocompatible. The lengths of the outer and inner tubes 4, 6 should not be excessive, as increased length in small diameter tubes is associated with high resistance to the gas flow. A cannula (not shown) can surround the outer tube 4 to guide the laryngeal bypass device 1 through the trachea, to a position where respiration can be most efficiently carried out.

At the end 8 of the outer tube 4 is preferably a sealing lock 13, which is a stopper-like member with an orifice defined therethrough for accepting the inner tube 6. Each of the outer and inner tubes 4, 6 are subsequently terminated in a luer-lock receptacle 12, 14. The luer-lock receptacle 12 connected to the outer tube 4 provides ease of connection to an aspiration source (not shown) and the luer-lock receptacle 14 connected to the inner tube 6 provides ease of connection to a ventilation, or jetting source (not shown). The inner tube 6 typically delivers a jet of high pressure oxygenated gas from the ventilation source. The outer tube 4 is at a reduced pressure due to the aspiration source, causing inspirated gas to be drawn from the lungs. The aspiration source and the ventilation source are further described with respect to FIG. 2A.

The other end 16 of outer tube 4, in one embodiment, has a plurality of apertures 20 defined therein. The apertures 20 aid the outer tube 4 in performing suction and aid in dissipating the high pressure jet injected into the trachea via the inner tube 6. The other end 18 of the inner tube 6, in one embodiment, terminates in a deformable barrier 22. The barrier 22 may be integrally formed with the inner tube 6 or affixed to the inner tube 6 by soldering or welding. The barrier 22 is preferably comprised of plurality of individual wires 24 that are under tension or are jointed at their midpoints (not shown). This construction ensures that the wires 24 are collapsed while resident within the outer tube 4, and when disposed outside of the outer tube 4, are in an expanded state. When in an expanded state, the barrier 22, in one embodiment, achieves a basket-shape, as shown. The barrier 22 prevents tissue in the trachea known as mucosa, from obstructing the outer tube 6 during aspiration and maintains the axial position of the jet within the trachea, thus preventing it from directly impinging on the tracheal wall.

Referring to FIG. 1B, the diameter of the trachea 2 is much larger than the diameter of the laryngeal bypass device 1, particularly the outer tube 4. In fact, it is preferred that the laryngeal bypass device 1 does not touch the trachea 2 or the cilia 3 within the trachea. In the embodiment shown the outer tube 4 preferably has an outer diameter of about 3 mm or less (e.g., 2.5 mm), and the inner tube 6 is preferably a 16G catheter, although other diameters and grades can be used. It is preferred that the diameters of the outer 4 and inner 6 are small to facilitate insertion into the sublaryngeal trachea and to allow the device to act as a needle rather than a tracheostomy-type tube. As shown in this figure, the outer tube 4 and the inner tube 6 are concentric and the barrier member 22 when deployed extends to a diameter greater than the diameter of the outer tube 4.

Figure 2A:
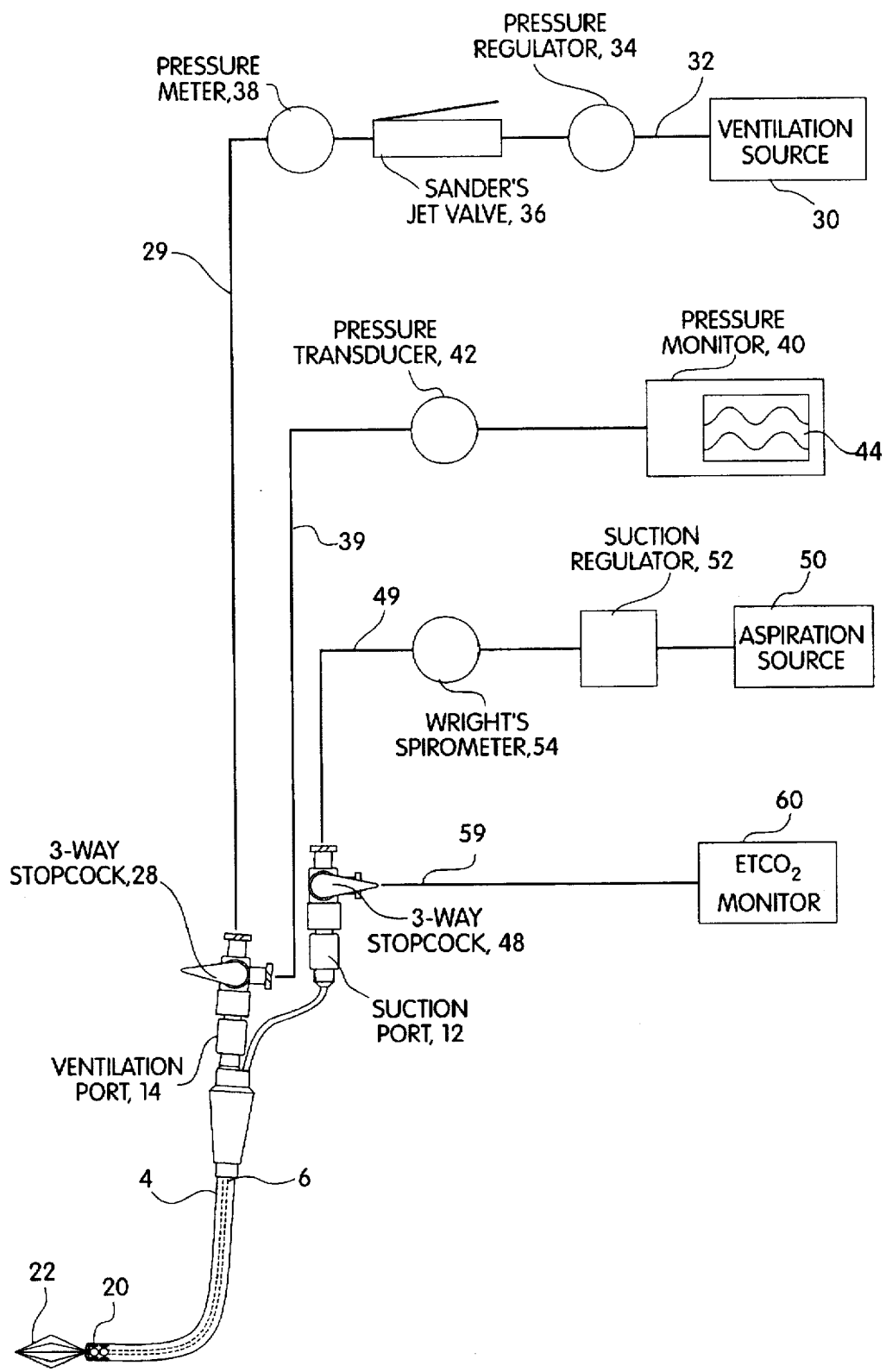
FIG. 2A shows the embodiment of the laryngeal bypass device of FIG. 1A and an embodiment of an associated ventilation system of the present invention.

Referring to FIG. 2A, the inner tube 6 and associated luer-lock receptacle 14 is connected via a three-way stopcock 28 and tubing 29 to a ventilation or jet source 30, such as an oxygen source for delivering a jet of oxygen through the inner tube 6. Alternatively, the jet of high pressure gas may comprise a mixture of other gases such as helium and oxygen to provide enhanced flow characteristics and therapeutic value. In this embodiment, the ventilation source can deliver gas at a pressures up to about 50 PSI. While a three-way stopcock 28 is shown, other fluid switching members can be used. Also associated with the ventilation source 30 is a pressure regulator 34, a jet valve 36, and a pressure meter 38, disposed at the output 32 of the ventilation source 30 to ensure that the pressure of the gas delivered does not exceed predefined limits. The jet valve 36 may be manually controlled or automatically controlled to intermittently activate the ventilation source 30 to deliver a jet of high pressure gas through the tubing 29 and into the inner tube 6.

The three-way stopcock 28 further couples the inner tube 6 to a pressure monitor 40 via tubing 39. The pressure monitor 40 is coupled to a pressure transducer 42 typically used for invasive blood pressure monitoring. Using the pressure monitor 40, pressure in the trachea can be monitored in real time, as the three-way stopcock 28 can be switched to open the port to the pressure transducer 42, allowing it to sense the pressure in the trachea during the period of time from the end of inspiration to the end of expiration. Alternatively, the pressure transducer 42 can be used to monitor continuously pressure in the trachea during the use of the laryngeal bypass device 1, as the stop-cock 28 can be configured such that it is open to both ports. The pressure monitor 40 further has a display 44 which allows medical personnel to evaluate visually the pressure in the trachea.

Still referring to FIG. 2A, the outer tube 4 and associated luer-lock receptacle 12 is connected via a three-way stopcock 48 and tubing 49 to an aspiration source 50. The aspiration source 50 is coupled to a Suction regulator 52 and a Wright's spirometer 54. The aspiration source 50 creates a negative pressure in the tubing 49 and the outer tube 4 that causes the gas delivered to the lungs to be removed from the lungs. The suction regulator 52 controls the pressure in the tubing 49 to ensure that a predefined negative pressure is not exceeded. The spirometer 54 is used to measure the tidal volume, which is a measure of the volume of gas passing into and out of the lungs, that is, the size of the difference between the volume delivered and the volume drawn. The tidal volume is further affected by such parameters as the diameter of the outer and inner tubes 4, 6, the pressure of the gas delivered by the inner tube 6, and the force of aspiration drawing gas into the outer tube 4.

The three-way stopcock 48 further couples the outer tube 4 via tubing 59 to a carbon dioxide monitor 60, shown in this figure as an end tidal carbon dioxide ($ETCO_2$) monitor. The carbon dioxide monitor 60 preferably monitors end tidal carbon dioxide ($ETCO_2$), which closely approximates the arterial partial pressure of $CO_2$. Carbon dioxide levels are preferably checked intermittently near the end of expiration by switching the three-way stopcock 48 to open the port to the carbon dioxide monitor 60. The operation of the above-described elements of the system is discussed in greater detail below.

Figure 2B:
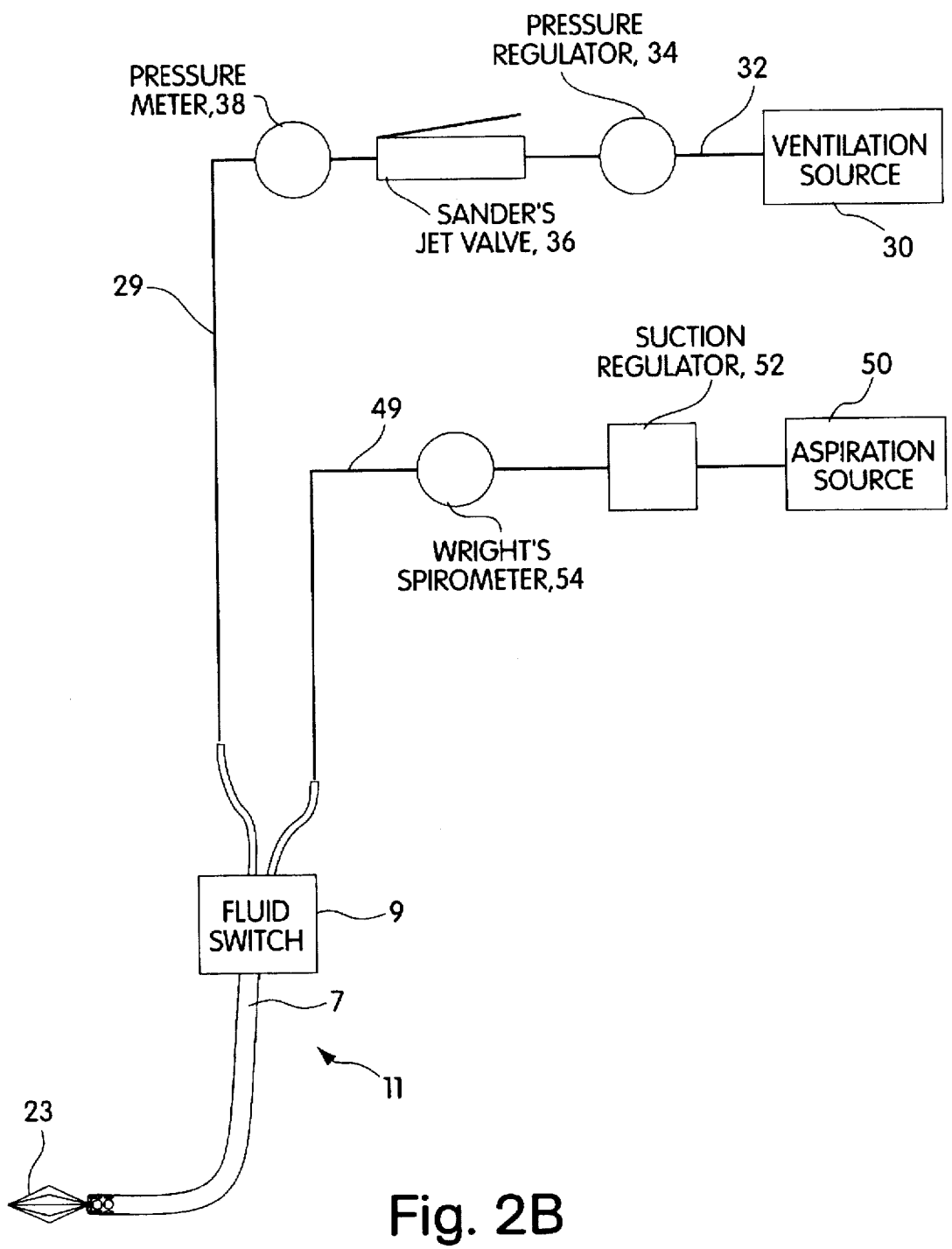
FIG. 2B shows an alternate embodiment of the laryngeal bypass device and an embodiment of an associated ventilation system of the present invention.

Referring to FIG. 2B, an embodiment of the laryngeal bypass device 11 utilizes a single tube 7 for aspiration and ventilation. By utilizing a single tube 7 adequate ventilation of the lungs occurs without the need for expiration of gas through the mouth, as the larynx is completely bypassed. High pressure jets of gas are alternately pushed into and pulled from the lungs, resulting in a novel "push-pull" effect which occurs sequentially.

The tube 7 which preferably has an outer diameter of about 3 mm or smaller (e.g., 2.5 mm), is inserted into the trachea and has a barrier member 23 formed at one end. The other end of tube 7 is coupled to a switching device 9, such as a fluid switch. The switching device 9 is fluidly coupled the tubing 29 and 49 such that when the switching device 9 is open to one tubing 29, 49, the other tubing 49, 29 is occluded. Tubing 29 is connected to a ventilation or jet source 30, as described above. Therefore, when the switching device 9 is open to tubing 29, a jet of gas travels through the tubing 29 to tube 7, and no aspiration occurs. Tubing 49 is connected to an aspiration source 50, as described above. Therefore, when the switching device 9 is open to tubing 49, a suction force exists in tubing 49 and tube 7, and no ventilation occurs. In this manner, the "push-pull" effect according to the invention is achieved in the single tube 7, but unlike other dual-tube embodiments, the ventilation and aspiration to occurs alternately. The ventilation source 30 is preferably coupled to a pressure regulator 34, a jet valve 36, and a pressure meter 38. Although not shown, a pressure monitor and pressure transducer may be utilized as described in connection with FIG. 2A. The aspiration source 50 is preferably coupled to a suction regulator 52 and a spirometer 54. Although not shown, an $ETCO_2$ monitor may be utilized as described in connection with FIG. 2A.

Figure 3:
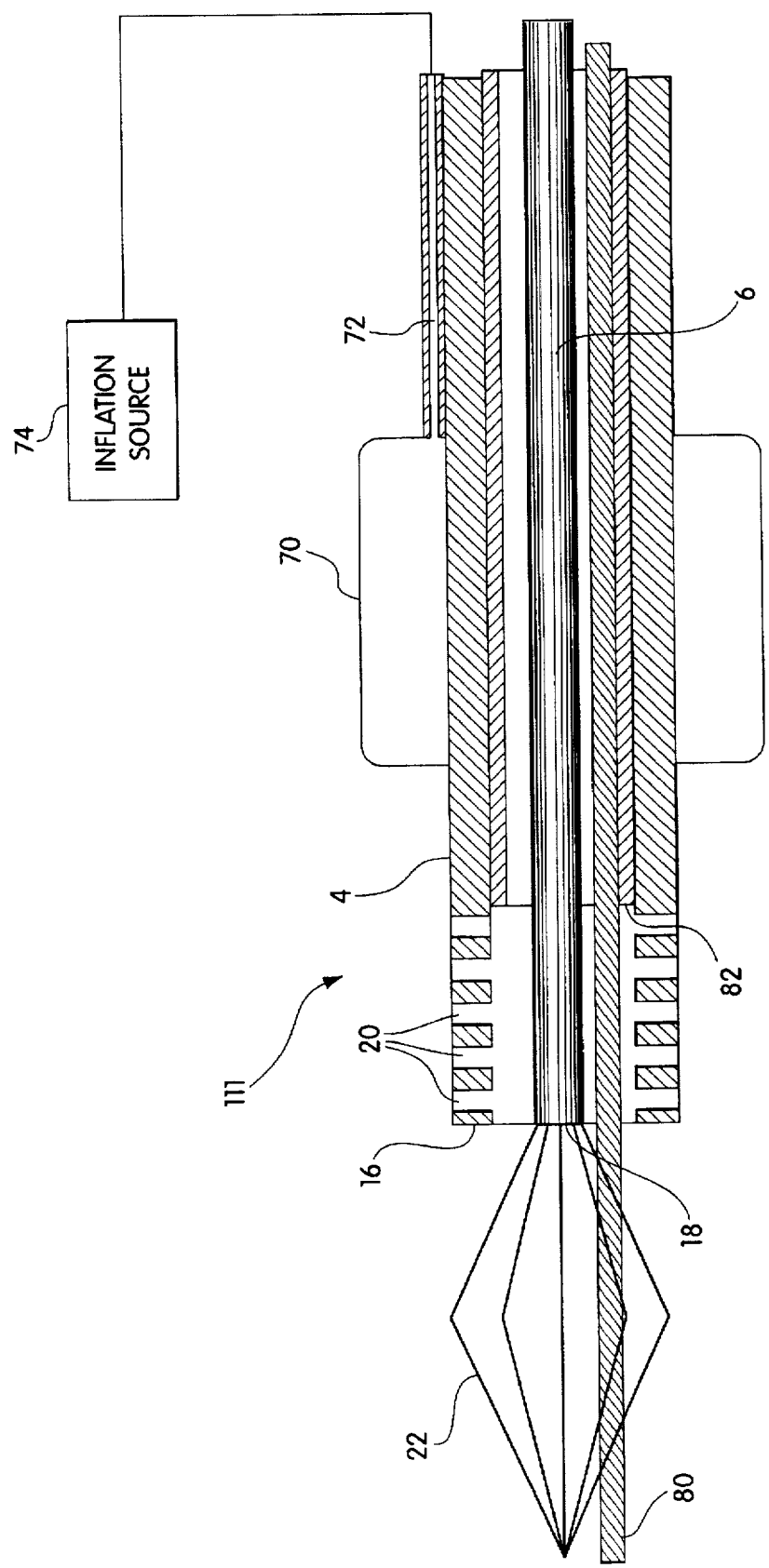
FIG. 3 shows an alternate embodiment of the laryngeal bypass device of the present invention, including an inflatable cuff and a guidewire.

Referring to FIG. 3, in an alternate embodiment, a laryngeal bypass device 111 includes an outer tube 4 having a plurality of apertures 20 at one end 16, an inner tube 6 having a barrier 22 disposed at the other end 18, and the outer tube 4 includes an inflatable cuff 70 encircling the outer tube 4 along its midsection. The inflatable cuff 70 is connected to an inflation tube 72, which delivers air from the inflation source 74 to the inflatable cuff 70. After the laryngeal bypass device 111 is inserted, the inflatable cuff 70 can be inflated to block the flow of air from the trachea to the larynx. By blocking the flow of air respiration is enhanced, and interference with a surgical procedure that may be taking place in the area of the larynx is further avoided. As further shown in this figure, a guidewire 80 is disposed within the outer tube 4 to guide the laryngeal bypass device 111 through the trachea. The guidewire 80 is preferably inserted prior to insertion of the outer tube 4, and can be slid out of the outer tube 4 after the outer tube 4 has been properly placed in the sublaryngeal trachea, as further described in the flow chart of FIG. 7. Additionally, the guidewire 80 can be used with an introducer 82 which preferably fits snugly within the outer tube 4.

Referring to FIG. 4A, in an alternate embodiment, an outer tube 104 and the inner tube 106 share a common section 108 of the wall 110 of the outer tube 104. This embodiment of the laryngeal bypass device 121 optimizes the internal space within the outer tube 104. The inner tube 106 terminates inside the outer tube 104 so that the distal end 116 of the outer tube 104 is not obstructed by the inner tube 106. By shortening the length of the inner tube 106 and having a multi-orificed ending in the tube 104, the suction force at the distal end 116 of the outer tube 104 is enhanced and the jet terminates in a more multi-orificed and safer pattern. A barrier 122 is formed at the distal end 116 of the outer tube 104. A cannula 130 is used to aid in insertion and placement of the laryngeal bypass device 121. The barrier 122 functions in a similar manner as described above with reference to FIG. 1A. When the laryngeal bypass device 121 is inserted into the trachea, the cannula 130 encircles the laryngeal bypass device 121. The barrier 122 is in a compressed state while disposed within the cannula 130. When the laryngeal bypass device 121 is properly placed within the trachea, the cannula 130 is removed and the barrier 122 achieves an expanded state. As described above, when the barrier 122 is in an expanded state, tissue is prevented from entering the outer tube 104 and the barrier 122 maintains axial flow. Referring to FIG. 4B, an end view of the inner tube 106 of the laryngeal bypass device 121 of FIG. 4A is shown as sharing a section 108 of the wall 110 of the outer tube 104. The barrier 122 preferably extends across the inside diameter of the outer tube 104. The cannula 130 has a greater diameter than the outside diameter of the outer tube 104.

Although the previous embodiments were described in terms of a small inner jet tube within a larger aspiration tube, other embodiments are possible. Referring to FIG. 5A, in an alternate embodiment of the laryngeal bypass device 211, an aspiration tube 204 is coupled externally with an inspiration tube 206. The inspiration tube 206 residing on the periphery of the aspiration tube 204, shares a section 208 of the wall 210 of the aspiration tube 204. The aspiration tube 204, like the outer tubes 4, 104 described in the above embodiments, preferably has an outside diameter of about 3 millimeters, and the inspiration tube 206, like the inner tubes 6, 106 described in the above embodiments, is preferably a 16G catheter. The inspiration tube 206 delivers gas to the lungs and the aspiration tube 204 draws gas from the lungs after inspiration has taken place. As there is little negative pressure exhibited on the opening 218 of the inspiration tube 206 due to its location external to the aspiration tube 204, a jet of pressurized gas can be delivered via the inspiration tube 206 to the trachea without losing gas volume. Referring to FIG. 5B, the aspiration tube 204 of the laryngeal bypass device 211 is shown as sharing section 208 of the outer wall 210 of the aspiration tube 204.

Figure 6A:
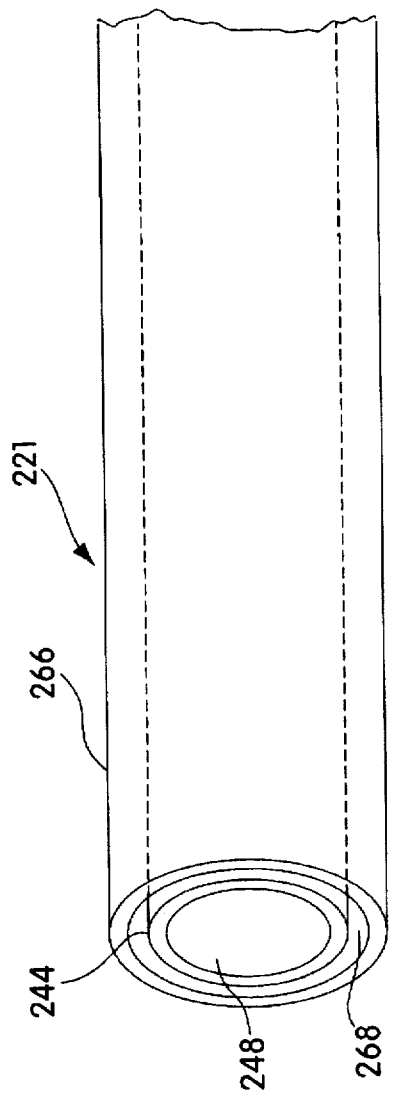
FIG. 6A shows an alternate embodiment of the laryngeal bypass device of the present invention wherein the ventilation tube encircles the aspiration tube.
Figure 6B:
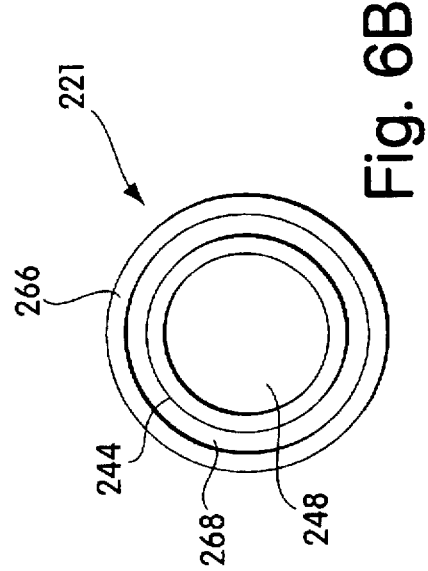
FIG. 6B is an end view of an alternate embodiment of the laryngeal bypass device of the present invention.

Referring to FIG. 6A, in an alternate embodiment of the laryngeal bypass device 221, the aspiration tube 244 is encircled by the ventilation tube 266. In this embodiment, a high pressure jet of gas is injected in the space 268 defined between the aspiration tube 244 and the ventilation tube 266, and the gas is aspirated through the aspiration tube 244. Referring to FIG. 6B, an end view of this embodiment shows the diameter of the ventilation tube 266 as slightly greater than the diameter of the inspiration tube 244. In this embodiment, for example, the ventilation tube 266 may have an outside diameter of about 3.5 millimeters and the aspiration tube 244 may have an outside diameter of about 2.5 millimeters. It is preferred that the diameters of the aspiration tube 244 and ventilation tube 266 are small to facilitate insertion into the sublaryngeal trachea and to allow the device to act as a needle rather than a tracheostomy-type tube. The space 268 between the ventilation tube 266 and the aspiration tube 244 for injecting gas is less than the space 248 within the aspiration tube 244 for aspirating gas.

Figure 7:
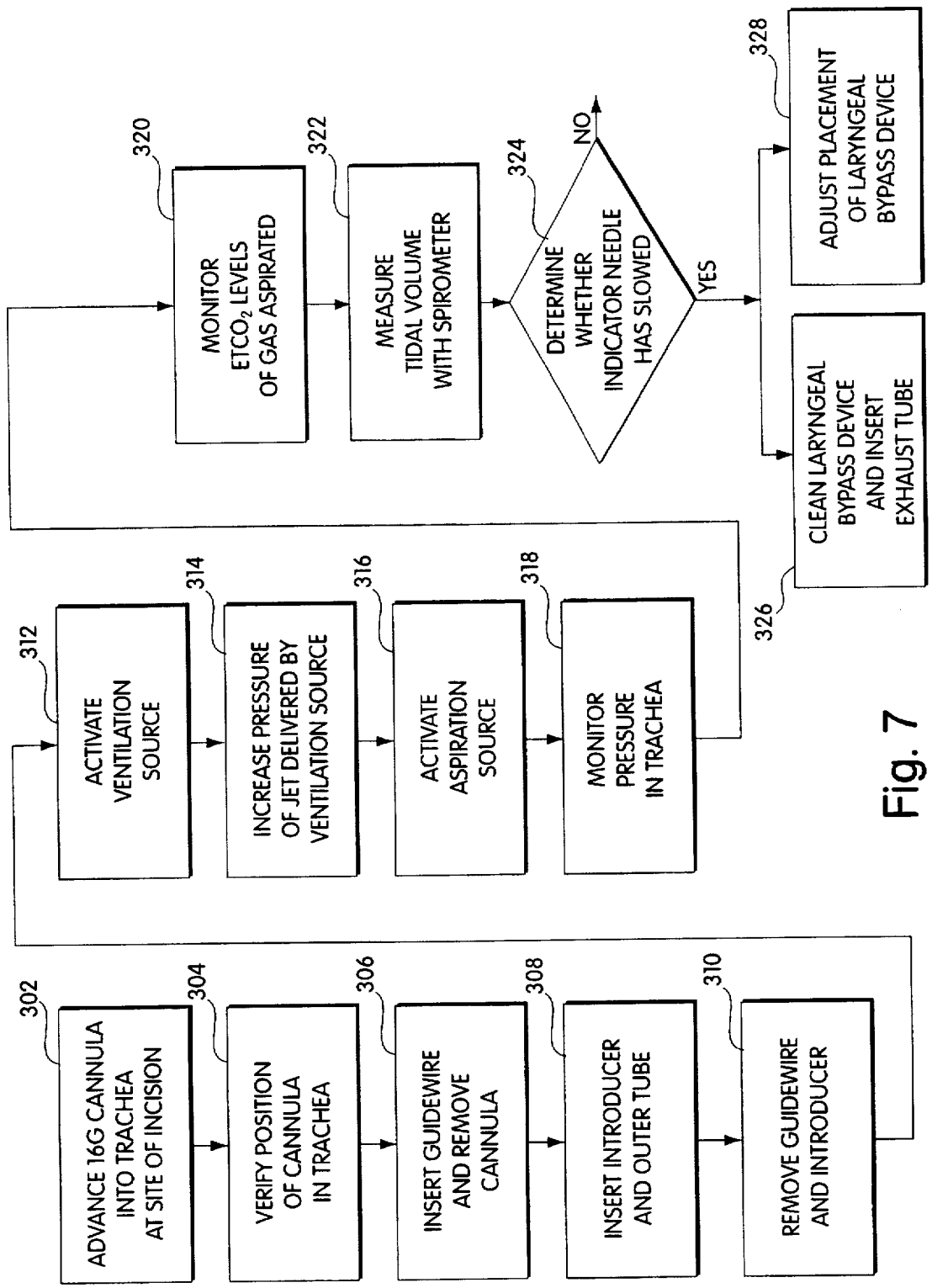
FIG. 7 shows a flow chart describing a method of using one embodiment of the laryngeal bypass device of the present invention.

Referring to the flow chart of FIG. 7, the embodiment of the laryngeal bypass device 1 and associated system as shown in FIG. 2A, operates as follows. As provided in step 302, a 16G cannula is advanced into the trachea sublaryngeally at the site of the incision. In step 304, the position of the cannula is verified as being within the trachea. This is typically carried out by inserting a 5 ml syringe having a few milliliters of water into the end of the cannula and pulling back on the syringe stopper. If the cannula is within the trachea, free aspiration of air through the water results. Water is preferably used, as bubbles are easily detected as air travels therethrough. Once the position of the device 1 is verified as proper, in step 306, a guidewire is then inserted at the site, and the cannula is removed. In step 308, an introducer is inserted along with the outer tube of the laryngeal bypass device, or if the introduction of the device is done through a separate plastic cannula then the plastic cannula with introducer is inserted over the guidewire. In step 310, the guidewire and introducer are removed. The introducer can be removed from the outer tube, or the introducing plastic cannula can be cut away over the outer tube. With either method, the inner tube can now be inserted into the outer tube.

In step 312 the ventilation source 30 is activated. In this step jet ventilation through the inner tube 6 is initiated at low pressure, preferably at about 5 PSI. During this time the aspiration source 50 is inactive. In step 314, the pressure of the jet ventilation is increased gradually to between 10 PSI to 20 PSI. As jet ventilation is increased, chest excursions are viewed and palpated by the physician, and breath sounds are auscultated. The pressure at which a high pressure jet is injected into the trachea is within a predefined range, preferably within 5 PSI–50 PSI. In step 316 the aspiration source 50 is activated, at a time judged to be appropriate based on clinical observations and pressure tracings, and the pressure in the outer tube 6 decreases which causes a suction force pulling gas from the lungs. The force at which gas is drawn from the lungs is also within a predefined range. Further, an inspiration to expiration ratio may be chosen so that the volume of gas delivered by the jet during the period of ventilation is greater than the volume drawn during that same period.

As provided in step 318, pressure in the trachea is monitored by opening the port on the three-way stopcock 28 that is in communication with tubing 39 leading to the pressure transducer 42. When the upper trachea is open to atmosphere and fully patent, after inspiration, a rapid drop of pressure to zero is shown on the display 44. In this case, the next jet ventilation does not have to commence immediately as lung volume will not drop significantly below functional residual capacity. If, however, the upper trachea or larynx is closed by tumor, scar tissue or packings, a much more gradual drop in pressure from peak to zero is shown on the display 44. In this case, it is important to commence the next jet inspiration after a zero pressure value is shown on the display. By beginning the next jet at zero pressure, breath stacking and negative pressure are avoided.

As provided in step 320, $ETCO_2$ levels are also intermittently monitored during respiration by opening the port on the stop-cock 48 that is in communication with the tubing 59 leading to the $ETCO_2$ monitor 60. The stopcock 48 is preferably switched to open near the end of expiration to make sure that the patient's lungs are near deflation, as this gives an end-tidal carbon dioxide ($ETCO_2$) reading which closely approximates arterial carbon dioxide ($CO_2$).

Tidal volume is measured during aspiration with the Wright Spirometer 54 as provided in step 322. The spirometer 54 has an indicator needle that is typically in constant motion. In step 324, a determination is made as to whether the motion of the indicator needle has slowed, as this may be a warning that the laryngeal bypass device 1 requires cleaning, for example, should clogging of the outer tube occur. If clogging of the outer tube occurs, the inner tube is removed and the outer tube is flushed with saline and/or de-clogged with a pipe cleaner-type device whose end is smoothed to avoid tracheal damage. Alternatively, the slowing of the indicator needle may indicate that the placement of the device 1 is near the tracheal wall and requires adjustment which can be carried out with careful manipulation using imaging equipment if necessary, as provided in step 328.

Having described the preferred embodiments and other embodiments of the invention, it will now become apparent to one of skill in the art that still other embodiments incorporating the concepts may be used. It is felt, therefore, that these embodiments should not be limited to the disclosed embodiments but rather should be limited only by the spirit and scope of the following claims.

What is claimed is:

1. A laryngeal bypass device adapted for transcutaneous insertion into a human trachea, comprising:
    a first tubular member having a first end and a second end, said first end couplable to an aspiration device, and said second end comprising a barrier member maintaining said second end free of human tissue; and
    a second tubular member having a first end and a second end, said first end couplable to an inspiration device;
    wherein said second tubular member injects air to the trachea and said first tubular member aspirates air from the trachea, transcutaneously.

2. The laryngeal bypass device according to claim 1, wherein said second tubular member is disposed within said first tubular member.

3. The laryngeal bypass device according to claim 2, wherein said first tubular member and said second tubular member are concentrically disposed.

4. The laryngeal bypass device according to claim 1 wherein said first tubular member is disposed within said second tubular member.

5. The laryngeal bypass device according to claim 4 wherein a space defined between said first tubular member and said second tubular member is less than a space defined within said first tubular member.

6. The laryngeal bypass device according to claim 1, wherein said barrier member maintains axial flow in the trachea.

7. The laryngeal bypass device according to claim 1, further comprising:
an inflatable cuff encircling said first and second tubular members, said inflatable cuff couplable to an inflation device.

8. The laryngeal bypass device according to claim 1, further comprising:
a guidewire and introducer disposed within said laryngeal bypass device.

9. The laryngeal bypass device according to claim 1, wherein said second tubular member is formed along the wall of said first tubular member.

10. The laryngeal bypass device according to claim 1, wherein said first tubular member is disposed within an intravascular cannula.

11. The laryngeal bypass device according to claim 1, wherein said first end of said first tubular member is couplable to the aspiration device via a luer lock, and said first end of said second tubular member is couplable to the inspiration device via a luer lock.

12. A laryngeal bypass device adapted for transcutaneous insertion into a human trachea, comprising:
a first tubular member having a first end and a second end, said first end couplable to an aspiration device, and said second end having a plurality of apertures formed therein; and
a second tubular member disposed within said first tubular member, said second tubular member having a first end and a second end, said second end comprising a barrier member maintaining said second end free of human tissue, and said first end couplable to an inspiration device;
wherein said second tubular member injects air to the trachea and said first tubular member aspirates air from the trachea, transcutaneously.

13. The laryngeal bypass device according to claim 12, further comprising:
an inflatable cuff encircling said first and second tubular members, said inflatable cuff couplable to an inflation device.

14. The laryngeal bypass device according to claim 12, further comprising:
a guidewire disposed within said first tubular member.

15. The laryngeal bypass device according to claim 12, wherein said second tubular member is formed along the wall of said first tubular member.

16. The laryngeal bypass device according to claim 12, wherein said first tubular member and said second tubular member are concentrically disposed.

17. The laryngeal bypass device according to claim 12, wherein said first tubular member is disposed within an intravascular cannula.

18. The laryngeal bypass device according to claim 12, wherein said first end of said first tubular member is couplable to the aspiration device via a luer lock, and said first end of said second tubular member is couplable to the inspiration device via a luer lock.

19. A laryngeal bypass device comprising:
a first tubular member adapted for transcutaneous insertion into a human trachea, having a second end and a first end;
an aspiration device coupled to said first end of said first tubular member;
a second tubular member concentrically disposed within said first tubular member, having a second end and a first end; and
a ventilation source coupled to said first end of said second tubular member;
whereby said second tubular member delivers air from said ventilation source to the trachea, and said first tubular member aspirates air from the trachea.

20. The laryngeal bypass device according to claim 19, wherein said ventilation source intermittently emits a jet of air.

21. The laryngeal bypass device according to claim 20, wherein said aspiration device continuously aspirates air.

22. The laryngeal bypass device according to claim 19, said second end of said second tubular member comprising a barrier member prohibiting entry of tissue into said first and second tubular members.

23. The laryngeal bypass device according to claim 22, wherein said barrier member is retractable when disposed within said first tubular member, and said barrier member is extendible when disposed outside said second end of said first tubular member.

24. The laryngeal bypass device according to claim 19, said second end of said first tubular member having a plurality of apertures formed therein.

25. The laryngeal bypass device according to claim 19, further comprising a pressure monitor coupled to said first end of said second tubular member.

26. The laryngeal bypass device according to claim 25, further comprising a carbon dioxide monitor coupled to said first end of said first tubular member.

27. The laryngeal bypass device according to claim 19, further comprising:
an inflatable cuff encircling said first tubular member; and
an air injection source coupled to said inflatable cuff, for inflating said inflatable cuff to block the flow of air to the larynx.

28. The laryngeal bypass device according to claim 19, further comprising:
a guidewire disposed with said first tubular member.

29. A laryngeal bypass device comprising:
a tubular member, having a diameter of approximately 3 millimeters, for transcutaneous insertion into the sublaryngeal trachea;
a ventilation source for delivering a jet of high pressure gas to the trachea through said tubular member;
an aspiration source for drawing gas from the trachea into said tubular member, wherein said sources alternately deliver to and draw from the trachea via said tubular member; and
a switching device coupling said tubular member to said ventilation source and said aspiration source, said switching device alternately providing to the trachea via said tubular member the jet from said ventilation source and suction from said aspiration source.

30. A method of using a laryngeal bypass device such that breathing is accomplished, comprising:
inserting transcutaneously into the sublaryngeal trachea a laryngeal bypass device comprising: a first tubular member for aspirating the lungs, and a second tubular member disposed within said first tubular member for inspirating the lungs;
delivering air through said second tubular member to inspirate the lungs; aspirating air through said first tubular member; and
preventing tissue from entering said first tubular member during aspiration.

31. A laryngeal bypass device adapted for transcutaneous insertion into a human trachea, comprising:

a first tubular member having a first end and a second end, said first end couplable to an aspiration device, said first tubular member being disposed within an intravascular cannula; and a second tubular member having a first end and a second end, said first end couplable to an inspiration device;

wherein said second tubular member injects air to the trachea and said first tubular member aspirates air from the trachea, transcutaneously.

32. The laryngeal bypass device according to claim 31, said second end of said first tubular member having a plurality of apertures formed therein.

33. A laryngeal bypass device adapted for transcutaneous insertion into a human trachea, comprising:

a first tubular member having a first end, a second end, and a diameter of approximately 3 millimeters, said first end couplable to an aspiration device; and a second tubular member disposed within said first tubular member, said second tubular member having a first end and a second end, said first end couplable to an inspiration device;

wherein said second tubular member injects air to the trachea and said first tubular member aspirates air from the trachea, transcutaneously.

34. A laryngeal bypass device adapted for transcutaneous insertion into a human trachea, comprising:

a first tubular member having a first end and a second end, said first end couplable to an aspiration device;

a second tubular member disposed within said first tubular member, said second tubular member having a first end and a second end, said second end comprising a barrier member maintaining said second end free of human tissue, and said first end couplable to an inspiration device; and a guidewire disposed within said first tubular member;

wherein said second tubular member injects air to the trachea and said first tubular member aspirates air from the trachea, transcutaneously.

35. A laryngeal bypass device adapted for transcutaneous insertion into a human trachea, comprising:

a first tubular member having a first end and a second end, said first end couplable to an aspiration device; and a second tubular member formed along a wall of said first tubular member, said second tubular member having a first end and a second end, said second end comprising a barrier member maintaining said second end free of human tissue, and said first end couplable to an inspiration device;

wherein said second tubular member injects air to the trachea and said first tubular member aspirates air from the trachea, transcutaneously.

36. A laryngeal bypass device adapted for transcutaneous insertion into a human trachea, comprising:

a first tubular member having a first end and a second end, said first end couplable to an aspiration device, said first tubular member being disposed within an intravascular cannula; and a second tubular member disposed within said first tubular member, said second tubular member having a first end and a second end, said second end comprising a barrier member maintaining said second end free of human tissue, and said first end couplable to an inspiration device;

wherein said second tubular member injects air to the trachea and said first tubular member aspirates air from the trachea, transcutaneously.

37. A laryngeal bypass device adapted for transcutaneous insertion into a human trachea, comprising:

a first tubular member having a first end and a second end, said first end couplable to an aspiration device via a first luer lock; and a second tubular member disposed within said first tubular member, said second tubular member having a first end and a second end, said second end comprising a barrier member maintaining said second end free of human tissue, and said first end couplable to an inspiration device via a second luer lock;

wherein said second tubular member injects air to the trachea and said first tubular member aspirates air from the trachea, transcutaneously.

38. A laryngeal bypass device comprising:

a first tubular member adapted for transcutaneous insertion into a human trachea, having a second end and a first end;

an aspiration device coupled to said first end of said first tubular member, said aspiration device continuously aspirating air;

a second tubular member disposed within said first tubular member, having a second end and a first end; and a ventilation source coupled to said first end of said second tubular member, said ventilation source intermittently emitting a jet of air;

whereby said second tubular member intermittently delivers air from said ventilation source to the trachea, and said first tubular member continuously aspirates air from the trachea.

39. A laryngeal bypass device comprising:

a first tubular member adapted for transcutaneous insertion into a human trachea, having a second end and a first end;

an aspiration device coupled to said first end of said first tubular member;

a second tubular member disposed within said first tubular member, having a second end and a first end, said second end comprising a barrier member prohibiting entry of tissue into said first and second tubular member, said barrier member being retractable when disposed within said first tubular member and extendible when disposed outside of the second end of said first tubular member; and a ventilation source coupled to said first end of said second tubular member;

whereby said second tubular member delivers air from said ventilation source to the trachea, and said first tubular member aspirates air from the trachea.

40. A laryngeal bypass device comprising:

a first tubular member adapted for transcutaneous insertion into a human trachea, having a second end and a first end;

an aspiration device coupled to said first end of said first tubular member;

a second tubular member disposed within said first tubular member, having a second end and a first end;

a ventilation source coupled to said first end of said second tubular member;

a carbon dioxide monitor coupled to said first end of said first tubular member; and a pressure monitor coupled to said first end of said second tubular member;

whereby said second tubular member delivers air from said ventilation source to the trachea, and said first tubular member aspirates air from the trachea.

41. A laryngeal bypass device comprising:

a tubular member, having a diameter of approximately 3 millimeters, for transcutaneous insertion into the sublaryngeal trachea;

a barrier member disposed at an end of said tubular member for preventing tissue from obstructing said tubular member;

a ventilation source for delivering a jet of high pressure gas to the trachea through said tubular member; and an aspiration source for drawing gas from the trachea into said tubular member, wherein said sources alternately deliver to and draw from the trachea via said tubular member.

42. The laryngeal bypass device according to claim 41, further comprising:

a switching device coupling said tubular member to said ventilation source and said aspiration source, said switching device alternately providing to the trachea via said tubular member the jet from said ventilation source and suction from said aspiration source.

* * * * *